(12) United States Patent
Fujii (10) Patent No.: US 9,808,223 B2
(45) Date of Patent: Nov. 7, 2017

(54) ULTRASOUND PROBE HAVING FIRST AND SECOND ROTATION TRANSMISSION SECTIONS

(71) Applicant: KONICA MINOLTA, INC., Chiyoda-ku, Tokyo (JP)

(72) Inventor: Kiyoshi Fujii, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 223 days.

(21) Appl. No.: 14/417,069

(22) PCT Filed: Jul. 19, 2013

(86) PCT No.: PCT/JP2013/004426
§ 371 (c)(1),
(2) Date: Jan. 23, 2015

(87) PCT Pub. No.: WO2014/017059
PCT Pub. Date: Jan. 30, 2014

(65) Prior Publication Data
US 2015/0201903 A1  Jul. 23, 2015

(30) Foreign Application Priority Data
Jul. 24, 2012 (JP) .................................. 2012-163376

(51) Int. Cl.
*A61B 8/00* (2006.01)
*A61B 8/08* (2006.01)
(Continued)

(52) U.S. Cl.
CPC ............ *A61B 8/4461* (2013.01); *A61B 8/483* (2013.01); *G10K 11/004* (2013.01); *G10K 11/355* (2013.01); *B06B 1/06* (2013.01)

(58) Field of Classification Search
CPC .. A61B 8/00; G10K 11/00; B06B 1/06; F16H 21/00
See application file for complete search history.

(56) References Cited

U.S. PATENT DOCUMENTS 4,913,158 A * 4/1990 Kikuchi ............... G10K 11/355
600/446
8,273,027 B2   9/2012 Hasegawa et al.
(Continued)

FOREIGN PATENT DOCUMENTS

| JP | 2009195305 A | 9/2009 |
|---|---|---|
| WO | 2008010558 A1 | 1/2008 |
| WO | 2010064415 A1 | 6/2010 |

OTHER PUBLICATIONS

Jacobs, J. E. "Ultrasound image converter systems utilizing electron-scanning techniques." IEEE Transactions on sonics and ultrasonics 15.3 (1968): 146-152.*
(Continued)

*Primary Examiner* — Long V Le
*Assistant Examiner* — Sean D Mattson
(74) *Attorney, Agent, or Firm* — Holtz, Holtz & Volek PC (57) ABSTRACT

An ultrasound probe includes: a first arm that swings along with rotation of a motor and includes a protrusion; a second arm that rotates along with rotation of a second gear engaged with a first gear attached to a first rotational shaft; a third arm attached to the second arm such that the third arm is rotatable with respect to the second arm; and an ultrasound device connected with the third arm. The protrusion of the first arm is connected with the third arm such that the protrusion is slidable on the third arm along the longitudinal direction of the third arm.

22 Claims, 10 Drawing Sheets

(51) Int. Cl.
   *G10K 11/00*   (2006.01)
   *G10K 11/35*   (2006.01)
   *B06B 1/06*    (2006.01)

(56) References Cited

U.S. PATENT DOCUMENTS

| | | | |
|---|---|---|---|
| 2009/0275836 A1* | 11/2009 | Fujii | A61B 8/13 600/459 |
| 2010/0076316 A1* | 3/2010 | Hasegawa | G01N 29/06 600/459 |
| 2011/0201937 A1* | 8/2011 | Fujii | A61B 8/14 600/459 |
| 2012/0065515 A1* | 3/2012 | Sato | A61B 8/12 600/459 |

OTHER PUBLICATIONS

Chinese Office Action (and English translation thereof) dated Feb. 22, 2016, issued in counterpart Chinese Application No. 201380038627.X.

International Search Report (ISR) dated Aug. 20, 2013 issued in International Application No. PCT/JP2013/004426.

\* cited by examiner

PRIOR ART

FIG. 18

ULTRASOUND PROBE HAVING FIRST AND SECOND ROTATION TRANSMISSION SECTIONS

TECHNICAL FIELD

The present invention relates to an ultrasound probe that mechanically scans a device.

BACKGROUND ART

To readily obtain in a short time a three-dimensional ultrasound diagnosis image of superficial tissues such as mammary gland, thyroid gland, carotid, body surface blood vessel and body surface for example, it is necessary to obtain a wide visual field region of an array type device in a region near the body surface, and to perform wide mechanical scanning along the shape of the body surface in a direction orthogonal to the scan direction of the array type device. In particular, with a hand carry type ultrasound probe, since three-dimensional images of various superficial tissues can be obtained with one three-dimensional ultrasound probe, it is possible to save diagnostic task of replacing probes, and to eliminate the need for using multiple three-dimensional ultrasound probes, which is great advantage in terms of cost. In addition, it is desirable to reduce the size of the shape of a probe as much as possible when the shape and position of diagnosis portions such as carotid thyroid gland are taken into consideration, for example. However, downsizing a three-dimensional ultrasound probe conflicts with increasing the three-dimensional diagnosis region.

Figure 18:
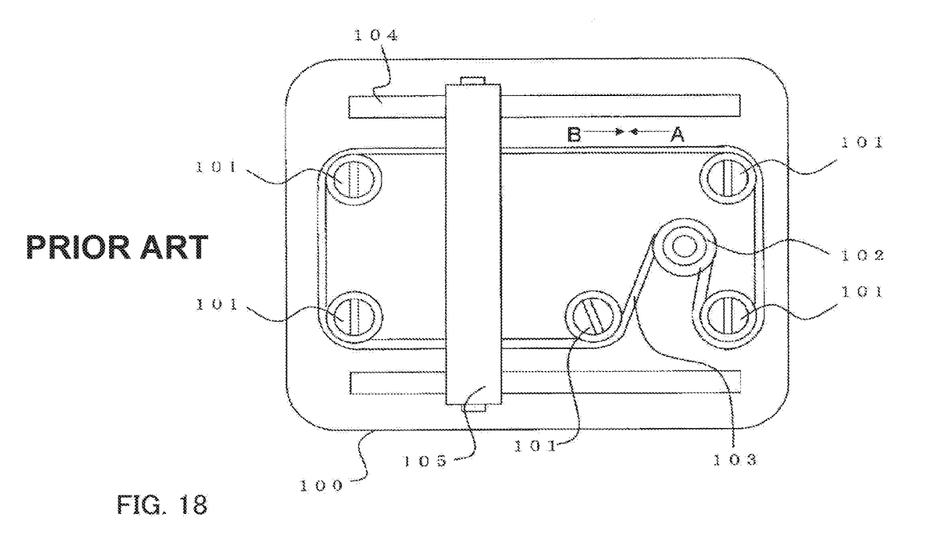
FIG. 18 illustrates a configuration of a conventional ultrasound probe.

Under such circumstances, a hand carry type three-dimensional ultrasound probe is known in which a mechanism that translates an ultrasound device by using a belt is applied to a hand carry type ultrasound probe, for example (see, for example, PTL 1). As illustrated in FIG. 18, the ultrasound probe disclosed in PTL 1 includes, in casing 100, five pulleys 101, timing pulley 102 provided with a flange which includes a toothed part on its outer periphery, belt 103 that surrounds pulleys 101 and 102, guide 104, and ultrasound device 105. Belt 103 reciprocates in direction A and direction B in the drawing when timing pulley 102 rotates, and ultrasound device 105 firmly fixed to belt 103 also reciprocates along guide 104.

CITATION LIST

Patent Literature

PTL 1
Japanese Patent Application Laid-Open No. 2009-195305

SUMMARY OF INVENTION

Technical Problem

In the ultrasound probe disclosed in PTL 1, however, pulleys 101 have to be disposed at both ends in the direction in which ultrasound device 105 moves. With such a structure, ultrasound device 105 cannot be moved in a space corresponding to the diameter of pulley 101. Consequently, the region in which the ultrasound probe makes contact with a living body is naturally greater than the region in which ultrasound device 105 mechanically moves according to the width of ultrasound device 105 and the diameter of pulley 101. As a result, in particular, depending on the shape and position of the diagnosis portion such as carotid and thyroid gland, for example, it may be difficult to attach an ultrasound probe to a desired location of an object portion of a living body because of the size of the ultrasound probe.

An object of the present invention is to provide a small-sized ultrasound probe which can achieve a wide scan region.

Solution to Problem

According to an embodiment of the present invention, an ultrasound probe includes: a probe casing in which acoustic coupling liquid is sealed; a motor fixed to the probe casing; a first arm fixed to a first rotational shaft, and configured to rotate along with rotation of the first rotational shaft; a protrusion provided to the first arm; a first rotation transmission section attached to the first rotational shaft; a second rotation transmission section engaged with the first rotation transmission section, and configured to rotate when the first rotation transmission section rotates in a direction opposite to a direction in which the first rotation transmission section rotates; a second rotational shaft fixed to the second rotation transmission section, and configured to serve as a rotational shaft of the second rotation transmission section; a second arm fixed to the second rotational shaft, and configured to rotate along with rotation of the second rotational shaft; a third arm attached to the second arm such that the third arm is rotatable with respect to the second arm; and an ultrasound device connected with the third arm, wherein: the first arm, the second arm and the third arm are located in the probe casing; the motor is connected with the first rotational shaft or the second rotational shaft; the first rotational shaft or the second rotational shaft connected with the motor rotates along with rotation of the motor; and the protrusion provided to the first arm is connected with the third arm such that the protrusion is slidable on the first arm along a longitudinal direction of the third arm.

Further, the second arm includes a first end and a second end different from the first end; the first end is connected with the probe casing such that the first end is rotatable with respect to the probe casing; the second end is connected with a first end portion of the third arm; the ultrasound device is connected with an end of a second end portion of the third arm different from the first end portion of the third arm; and the protrusion is located between the first end portion and the ultrasound device in the third arm.

Further, the third arm is provided with a guide portion extending along the longitudinal direction of the third arm; and the protrusion is in sliding contact with the guide portion.

Further, the guide portion is a part that is obtained by forming at least a portion of the third arm into a groove shape; and the protrusion is in sliding contact with an inner wall of the guide portion having the groove shape.

Further, the inner wall of the guide portion having the groove shape or the protrusion, or both is provided with a material that reduces a frictional resistance between a surface of the inner wall of the guide portion having the groove shape and a surface of the protrusion in contact with each other.

Further, the protrusion is provided with a bearing that is rotatable with respect to the protrusion.

Further, the ultrasound probe further includes: an elastic member attached to the first arm; a rotatable rotation plate on which a rotational force in one direction is exerted by the elastic member; and at least two bearings rotatably provided to the rotation plate, wherein the bearings are configured to make contact with the inner wall of the guide portion having the groove shape.

Further, the protrusion includes at least two protrusions; and the at least two protrusions sandwich the third arm.

Further, each of the at least two protrusions or the third arm, or both is provided with a material that reduces a frictional resistance between the surface of the third arm and surfaces of the at least two protrusions in contact with each other.

Further, the at least two protrusions are each provided with a bearing.

Further, the at least two protrusions pull against each other with an elastic member therebetween.

Further, the protrusion includes a slide bearing that is slidable on the third arm.

Further, the first rotation transmission section and the second rotation transmission section are each composed of a gear.

Further, the first rotation transmission section and the second rotation transmission section are each composed of a pulley; and a belt is wound around the first rotation transmission section and the second rotation transmission section such that the belt intersects between the first rotation transmission section and the second rotation transmission section.

Further, the first rotation transmission section and the second rotation transmission section are housed in the probe casing.

Further, the ultrasound device is connected with the third arm such that the ultrasound device is rotatable with respect to the third arm; the ultrasound device is connected with a guide shaft; a rail is provided in the probe casing; and the guide shaft is in contact with the rail such that the guide shaft is movable along the rail.

Further, the rail has a groove shape; and the guide shaft is located in a groove having the groove shape.

Further, the ultrasound probe further includes a second guide shaft connected with the guide shaft with an elastic member therebetween, wherein the guide shaft and the second guide shaft are sandwiched by the rail.

Further, the ultrasound probe further includes a second guide shaft connected with the guide shaft with an elastic member therebetween, wherein: the rail includes a protrusion; and the guide shaft and the second guide shaft sandwich the protrusion of the rail.

Further, in the guide shaft, a part that makes contact with the rail is provided with a bearing.

Further, the guide shaft or the rail or both is provided with a resin material that reduces a frictional resistance between the guide shaft and the rail in contact with each other.

Further, the ultrasound device is an electron scan type device; and the ultrasound device mechanically swings in a direction orthogonal to a direction of an electron scan of the ultrasound device.

Advantageous Effects of Invention

According to the ultrasound probe of an embodiment of the present invention, an ultrasound device can be mechanically swung by a small-sized swing mechanism at a large swing curvature or along a straight-line, and thus downsizing of a hand carry type ultrasound probe can be achieved. Consequently, an ultrasound probe with improved operability during diagnosis can be achieved. In particular, a wide visual field region in a region near the body surface, which is desired for ultrasound probes for diagnosis of superficial tissues, can be achieved with a small-sized lightweight ultrasound probe.

DESCRIPTION OF EMBODIMENT

Figure 1A:
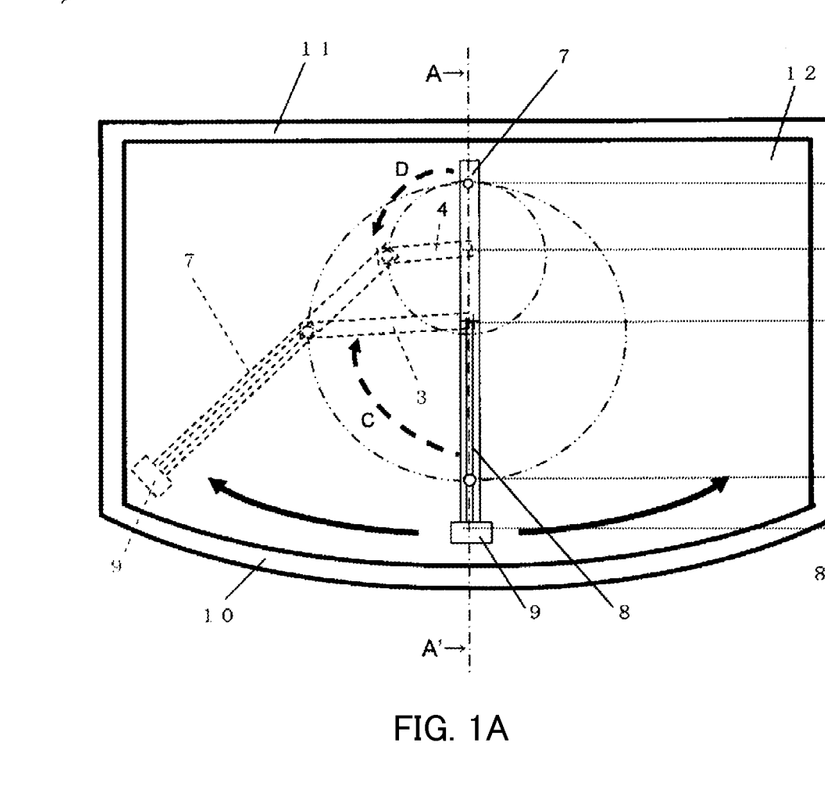
FIGS. 1A and 1B illustrate an ultrasound probe of an embodiment of the present invention.
Figure 1B:
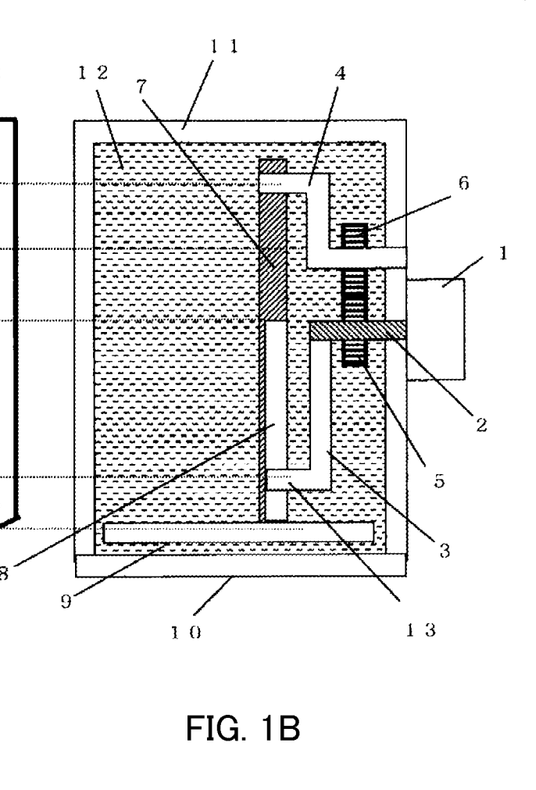

In the following, an embodiment of the present invention will be described with reference to the drawings. FIGS. 1A and 1B illustrate an ultrasound probe of the embodiment of the present invention. FIG. 1A is a front view of an ultrasound probe. FIG. 1B is a sectional view of the ultrasound probe illustrated in FIG. 1A taken along line A-A'. The ultrasound probe is connected with an ultrasound diagnostic apparatus main body not illustrated, and an electric drive signal is sent from the main body.

A rotational shaft of motor 1 fixed to probe casing 11, or, when motor 1 is provided with a deceleration mechanism, an output shaft of a deceleration mechanism (hereinafter referred to as "rotational shaft 2") penetrates probe casing 11. Rotational shaft 2 is rotated forward or backward at a predetermined angle in acoustic coupling liquid 12 that is encapsulated with an oil seal not illustrated, window 10, probe casing 11 and the like. Here, acoustic coupling liquid 12 facilitates propagation of ultrasound waves. As a result, first arm 3 having an end fixed to rotational shaft 2 is rotated forward or backward about rotational shaft 2 at a predetermined angle along with the rotation of rotational shaft 2, thus performing swing operation. First arm 3 includes: a part which extends in a direction perpendicular to rotational shaft 2 and is fixed to rotational shaft 2 at a portion thereof; and protrusion 13 that extends in parallel to rotational shaft 2 in a direction opposite to rotational shaft 2 and is connected with the other end of the part. It is to be noted that rotational shaft 2 may be a part of first arm 3. That is, a part of first arm 3 may be referred to as rotational shaft 2 fixed to first arm 3. In addition, protrusion 13 may be a part of first arm 3, and may be formed of a member different from that of first arm 3 and connected with first arm 3. The dotted line C shown in FIG. 1A represents a path of protrusion 13 in the case where first arm 3 performs swing operation along with the rotation of rotational shaft 2.

Second arm 4 is rotatably attached to probe casing 11. First gear 5 serving as a rotation transmission section is fixed to rotational shaft 2, and second gear 6 serving as a rotation transmission section is fixed to second arm 4. First gear 5 and second gear 6 engage with each other. That is, first gear 5 and second gear 6 mesh with each other, and, along with a rotational movement of rotational shaft 2, second arm 4 performs swing operation simultaneously with first arm 3 in the direction opposite to that of first arm 3. While first gear 5 and second gear 6 have the same size in FIGS. 1A and 1B, first gear 5 and second gear 6 may have different sizes.

Third arm 7 is attached to an end portion, which is different from the point in contact with probe casing 11, of second arm 4 such that third arm 7 is rotatable with respect to second arm 4. Along with the rotation of second gear 6, second arm 4 is rotated forward or backward at a predetermined angle about the rotational shaft of second gear 6, thus performing swing operation. Second arm 4 includes: a first portion that serves as a the rotational shaft of second gear 6 and extends perpendicularly to probe casing 11 from the point in contact with probe casing 11; a second portion that extends perpendicularly to the first portion; and a third portion that extends in a direction parallel to the first portion and opposite to the direction of the first portion. It is to be noted that the first portion of second arm 4 is connected with the rotational center of second gear 6. While the first portion of second arm 4 is the rotational shaft of second gear 6 in the configuration illustrated in FIGS. 1A and 1B, the rotational shaft of second gear 6 may be composed of a different member, and connected with second arm 4. In addition, the third portion may be composed of a member different from the second portion, and connected with the second portion. That is, the first portion of second arm 4 may be referred to as the rotational shaft fixed to second arm 4. In the case where first arm 3 performs swing operation along with the rotation of rotational shaft 2, protrusion 13 moves along the path represented by dotted line C in FIG. 1A. Then, third arm 7 performs swing operation along with the movement of protrusion 13. It is to be noted that, when second gear 6 rotates along with the rotation of rotational shaft 2, second arm 4 performs swing operation along with the rotation of the rotational shaft of second gear 6. It is to be noted that dotted line D in FIG. 1A represents the path of the point at which second arm 4 is coupled with third arm 7 in the case where second arm 4 performs swing operation along with the rotation of the rotational shaft of second gear 6.

It is to be noted that, in FIG. 1A, third arm 7 in a perpendicular state is represented by a solid line. Third arm 7 swings leftward and rightward, and in FIG. 1A, the dotted line represents third arm 7 swinging leftward.

Ultrasound device 9 is attached to an end portion of third arm 7 which is different from the point at which second arm 4 is coupled with third arm 7. Ultrasound device 9 can convert an electric signal to an ultrasound signal and vice versa. Ultrasound device 9 transmits and receives electric signals to and from the ultrasound diagnostic apparatus main body through a flexible printed board not illustrated.

As illustrated in FIG. 1B, third arm 7 includes, in its longitudinal direction, a first end portion at which second arm 4 is coupled with third arm 7, and a second end portion at which ultrasound device 9 is attached to third arm 7. Second gear 6 connected with second arm 4 is disposed at a position nearer to the first end portion at which second arm 4 is coupled with third arm 7, than first gear 5. In addition, in the direction in which rotational shaft 2 extends, third arm 7 is disposed at a position remote from motor 1 relative to first gear 5. In addition, the portion of first arm 3 that extends perpendicularly to rotational shaft 2 is disposed at a position between first gear 5 and third arm 7 in the direction in which rotational shaft 2 extends. Likewise, the second portion of second arm 4 is disposed at a position between third arm 7 and first gear 5 or second gear 6 in the direction in which rotational shaft 2 extends.

Figure 2:
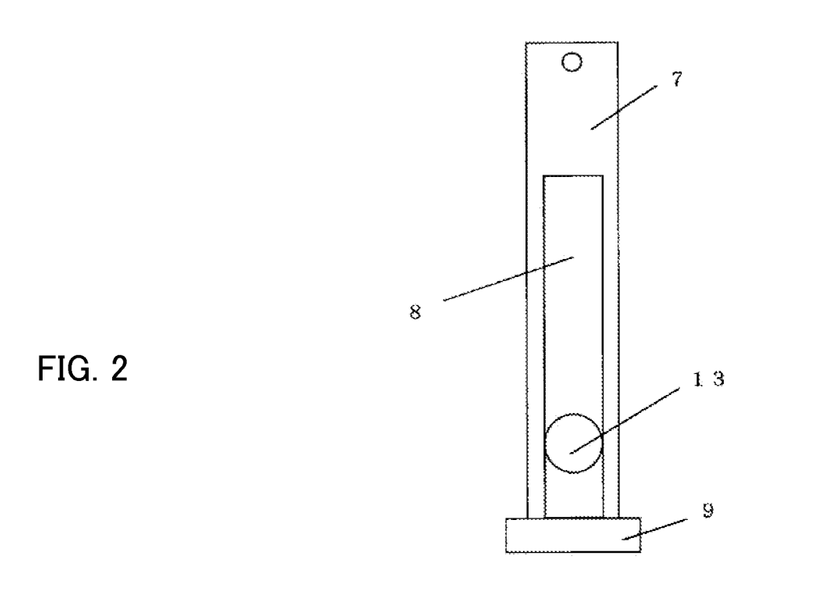
FIG. 2 illustrates an example of a sliding contact state represented by a solid line in FIG. 1A between a third arm and a protrusion of a first arm.

FIG. 2 illustrates an example of a sliding contact state between protrusion 13 of first arm 3 and third arm 7 represented by the solid line in FIG. 1A. As illustrated in FIG. 2, in third arm 7, longitudinal groove-shaped guide portion 8 is provided between the fixing end at which ultrasound device 9 is attached to third arm 7 and the part at which second arm 4 is coupled with third arm 7. In addition, protrusion 13 extending in parallel to rotational shaft 2 of first arm 3 makes sliding contact with the inner wall of guide portion 8. The width of the groove of guide portion 8 is substantially the same as the width of the portion of protrusion 13 that makes sliding contact with guide portion 8. The groove of guide portion 8 is a longitudinal groove extending along the longitudinal direction of third arm 7. It suffices that the length of the groove allows third arm 7 to move when third arm 7 swings leftward and rightward along with a forward or backward rotation of rotational shaft 2 at a predetermined angle as illustrated in FIG. 1A. Along with the forward or backward rotations of first arm 3 and second arm 4 in opposite directions in response to the rotational movement of rotational shaft 2, protrusion 13 located at the inner wall of guide portion 8 of third arm 7 rotates while moving along the groove of guide portion 8. That is, protrusion 13 of first arm 3 makes sliding contact with the inner wall of guide portion 8 such that protrusion 13 translates in the longitudinal direction of third arm 7. While the above-mentioned guide portion 8 is composed of a groove formed in a part of third arm 7, the guide portion 8 may be composed of a member different from third arm 7.

First arm 3 fixed to rotational shaft 2, and second arm 4 that is rotated by second gear 6 engaged with first gear 5 fixed to rotational shaft 2 always rotate in opposite directions in response to a forward or backward rotation of rotational shaft 2. Along with the rotation of rotational shaft 2, the coupling point between second arm 4 and third arm 7 moves and protrusion 13 slides along the longitudinal direction of third arm 7. Thus, ultrasound device 9 attached to third arm 7 moves along a track different from the track that is obtained when the case where the coupling point between third arm 7 and second arm 4 is a fixed rotational shaft.

It is to be noted that first gear 5 and second gear 6 may be disposed on the outside of probe casing 11. It is preferable to dispose first gear 5 and second gear 6 on the inside of probe casing 11 and window 10. One reason for this is that, when first gear 5 and second gear 6 are disposed on the inside of probe casing 11 and window 10, the shaft that penetrates probe casing 11 is only rotational shaft 2, and therefore it is only necessary to provide an oil seal or the like, which is provided at the penetrating portion for sealing acoustic coupling liquid 12, at one place. In addition, it is not necessary to fill the entire space surrounded by probe casing 11 and window 10 with acoustic coupling liquid 12, and it is only necessary that acoustic coupling liquid 12 presents between swinging ultrasound device 9 and the window.

While motor 1 is connected with rotational shaft 2 in the configuration illustrated in FIGS. 1A and 1B, motor 1 may be connected with the above-described first portion of second arm 4.

Figure 3:
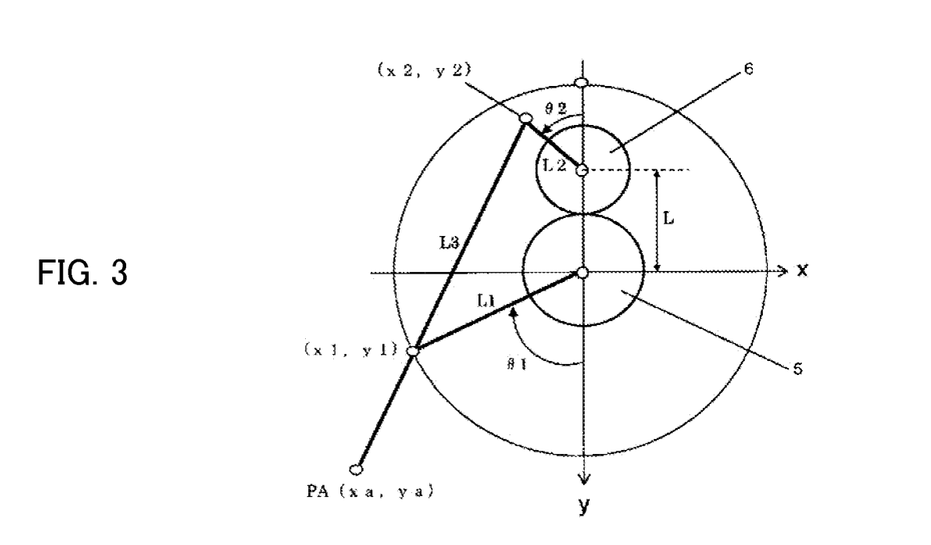
FIG. 3 illustrates operation of a swing mechanism of the embodiment of the present invention.

FIG. 3 describes operation of a swing mechanism composed of first arm 3, second arm 4, third arm 7, first gear 5 and second gear 6. In the following, with reference to FIG. 3, a swing rotation is described in detail. In the following description, the lengths of first arm 3, second arm 4, and third arm 7 are represented by L1, L2 and L3, respectively, and the distance between the rotational center of first arm 3 and the rotational center of second arm 4 is represented by L, as illustrated in FIG. 3. Regarding swing angle θ1 of first arm 3, the clockwise direction in FIG. 3 is defined as positive direction, and the counter clockwise direction in FIG. 3 is defined as negative direction. Conversely, regarding swing angle θ2 of second arm 4, the counterclockwise direction in FIG. 3 is defined as positive direction, and the clockwise direction is defined as negative direction. It is to be noted that the 0-degree positions of angles θ1 and θ2 are on the lower side of the vertical line of FIG. 3.

When the swing operations of first arm 3 and second arm 4 are interlocked with first gear 5 and second gear 6, second arm 4 is rotated by angle θ2 in the direction opposite to that of first arm 3. Angle θ2 is expressed by Expression (1).

[Expression 1]

$$\theta2=\theta1\times(\text{number of teeth of first gear})/(\text{number of teeth of second gear}) \quad (1)$$

The position of the end of first arm 3 (x1, y1) about the rotational center of first arm 3 in the xy-plane illustrated in FIG. 3 is expressed by Expression (2).

[Expression 2]

$$x1=-L1\times\sin(\theta1/180\times\pi)$$
$$y1=L1\times\sin((\theta1-90)/180\times\pi) \quad (2)$$

In addition, the position of the end of second arm 4 (x2, y2) about the rotational center of second arm 4 having length L2 in the xy-plane illustrated in FIG. 3 is expressed by Expression (3).

[Expression 3]

$$x2=-L2\times\cos((\theta2-90)/180\times\pi)=2\times\cos((\theta2+90)/180\times\pi)$$
$$y2=L2\times\sin(\theta2+90/180\times\pi) \quad (3)$$

In the case where the rotational center of second arm 4 is the origin, the position of the end of first arm 3 (x1, y1) is expressed by Expression (4).

[Expression 4]

$$x1=-L1\times\sin(\theta1/180\times\pi)$$
$$y1=L1\times\sin((\theta1-90)/180\times\pi)-L \quad (4)$$

When the starting point (x2, y2), the point (x1, y1) on the line segment of third arm 7 having length L3, and the length of line segment L3 are set, end position PA (xa, ya) of third arm 7 can be computed as described below. Here, the origin of PA (xa, ya) is the rotational center of second arm 4.

The length of line segment L3 is expressed by Expression (5).

[Expression 5]

$$L3=\sqrt{((xa-x2)(xa-x2)+(ya-y2)(ya-y2))} \quad (5)$$

When the slope of line segment L3 is represented by m, slope m is expressed by Expression (6).

[Expression 6]

$$m=(ya-y2)/(xa-x2)=(y1-y2)/(x1-x2) \quad (6)$$

It should be noted that the case of x2=x1 is excepted since division is not allowed in the case of x2=x1 in Expression (6).

Expression (7) is obtained from Expression (6).

[Expression 7]

$$xa=-1/m(ya-y2)+x2$$
$$ya=m(xa-x2)+y2 \quad (7)$$

Expression (7) is used for substitution in Expression (5) to compute end position PA (xa, ya) of third arm 7.

Figure 4:
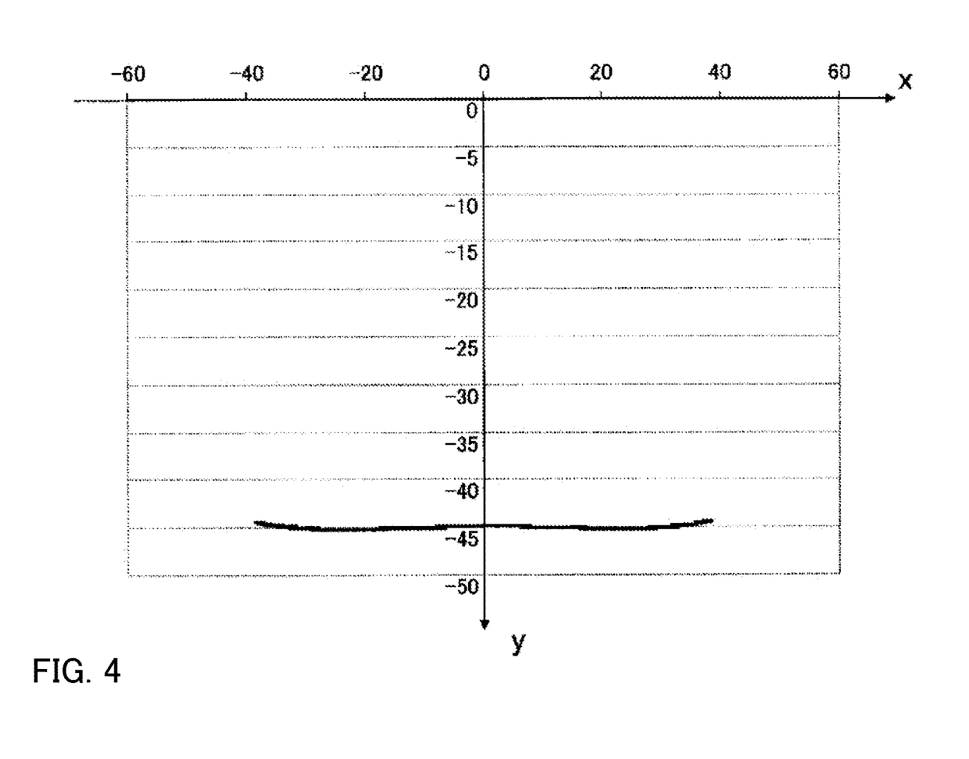
FIG. 4 illustrates an example of a track of end position PA of third arm 7.

FIG. 4 illustrates an example of a track of end position PA of third arm 7 when first arm 3 is swung ±45 degrees relative to y axis with a configuration in which length L1 of first arm 3 is 15 mm, length L2 of second arm 4 is 50 mm, length L3 of third arm 7 is 60 mm, the numbers of teeth of first gear 5 and second gear 6 are equal to each other, and distance L between the rotational center of first arm 3 and the rotational center of second arm 4 is 15 mm. As described above, ultrasound device 9 is attached to the end of third arm 7, and thus, in the example illustrated in FIG. 4, ultrasound device 9 can be substantially horizontally moved in x-axis direction.

The track of end position PA of third arm 7 illustrated in FIG. 4 is merely an example, and desired tracks of end position PA of third arm 7 can be achieved by changing the lengths of L1, L2 and L3, and the gear ratio (teeth number ratio) between first gear 5 and second gear 6.

Figure 5:
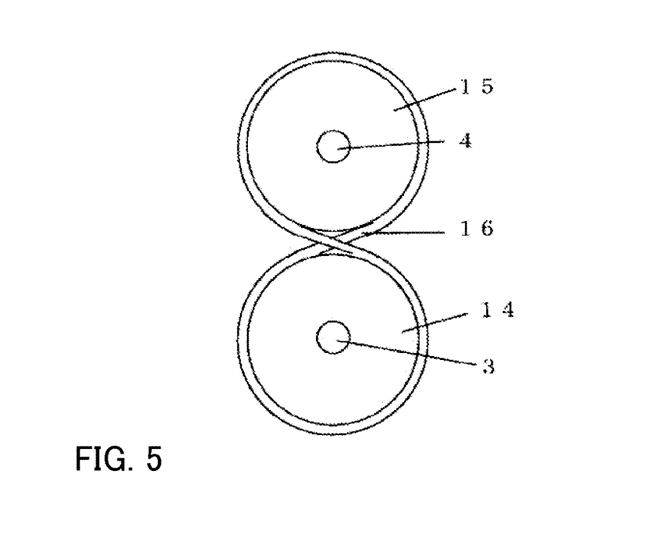
FIG. 5 illustrates an example of a rotation transmission section of the embodiment of the present invention.

As illustrated in FIG. 5, it is also possible to adopt a configuration in which, in place of first gear 5 and second gear 6, first pulley 14 and second pulley 15 are attached to first arm 3 and second arm 4, and first pulley 14 and second pulley 15 are coupled together by belt 16. In this case, continuous belt 16 is wound around first pulley 14 and second pulley 15 such that belt 16 intersects between first pulley 14 and second pulley 15. With belt 16, second pulley 15 rotates along with first pulley 14 when first pulley 14 rotates. When a steel belt is used as belt 16, it is possible to reduce backlash which may frequently occur at a coupling part of gears.

In the following, specific configurations of the sliding contact state of third arm 7 and protrusion 13 provided at an end of first arm 3 are described with some examples. In either case, protrusion 13 of first arm 3 is connected with third arm 7 such that protrusion 13 can be translated along the longitudinal direction of third arm 7.

Figure 6:
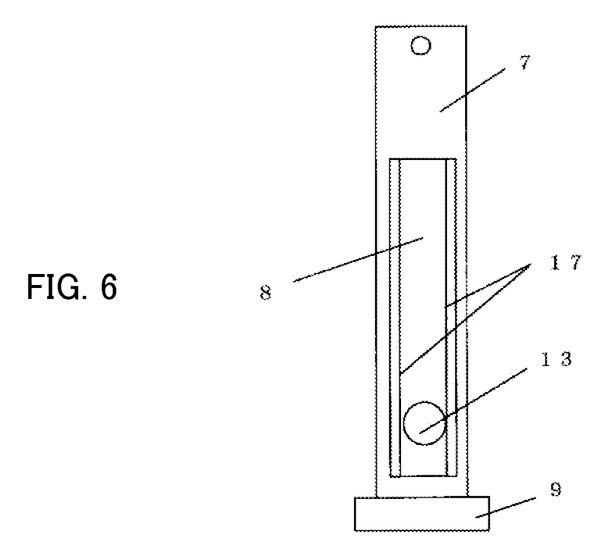
FIG. 6 illustrates an example of a sliding contact state between the third arm and the protrusion of the first arm.

FIG. 6 illustrates an example of a sliding contact state between groove-shaped guide portion 8 provided in third arm 7 and protrusion 13 provided at an end of first arm 3. The sliding contact state of protrusion 13 may be achieved with a configuration illustrated in FIG. 6 instead of the sliding contact state illustrated in FIG. 2. In the configuration illustrated in FIG. 6, protrusion 13 is positioned so as to be sandwiched by groove-shaped guide portion 8. In order that protrusion 13 smoothly slides on guide portion 8, the inner wall of guide portion 8 or protrusion 13 or both is preferably coated with low friction resin 17 composed of a fluorine resin such as polytetrafluoroethylene. With such a configuration, the frictional resistance between the side wall of guide portion 8 and the surface of protrusion 13 in contact with each other is reduced.

Figure 7:
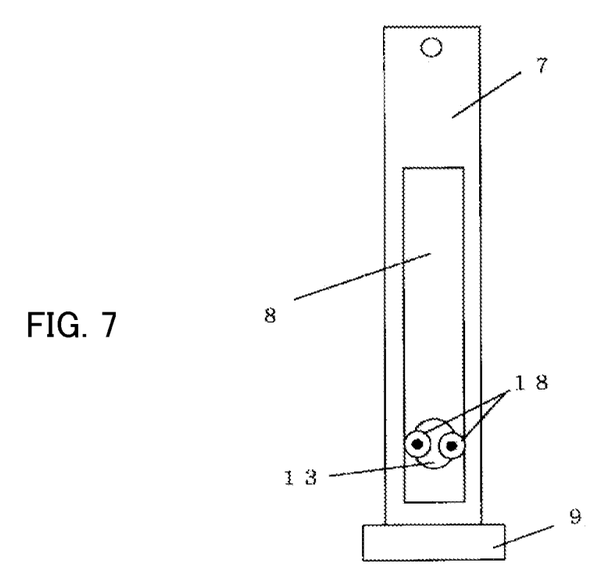
FIG. 7 illustrates an example of a sliding contact state between a groove-shaped guide portion provided to the third arm and the protrusion of the first arm.

FIG. 7 illustrates an example of the sliding contact state between groove-shaped guide portion 8 provided in third arm 7 and protrusion 13 provided at an end of first arm 3. The sliding contact state of protrusion 13 may be achieved with the configuration illustrated in FIG. 7 instead of the configuration illustrated in FIG. 2. In the configuration illustrated in FIG. 7, protrusion 13 is positioned so as to be sandwiched by groove-shaped guide portion 8. In order that protrusion 13 further smoothly slides on guide portion 8, it is preferable to adopt a configuration in which protrusion 13 is provided with two or more bearings 18 that make contact with the both ends of guide portion 8. It is also possible to coat the inner wall of groove-shaped guide portion 8 with low friction resin 17.

Figure 8A:
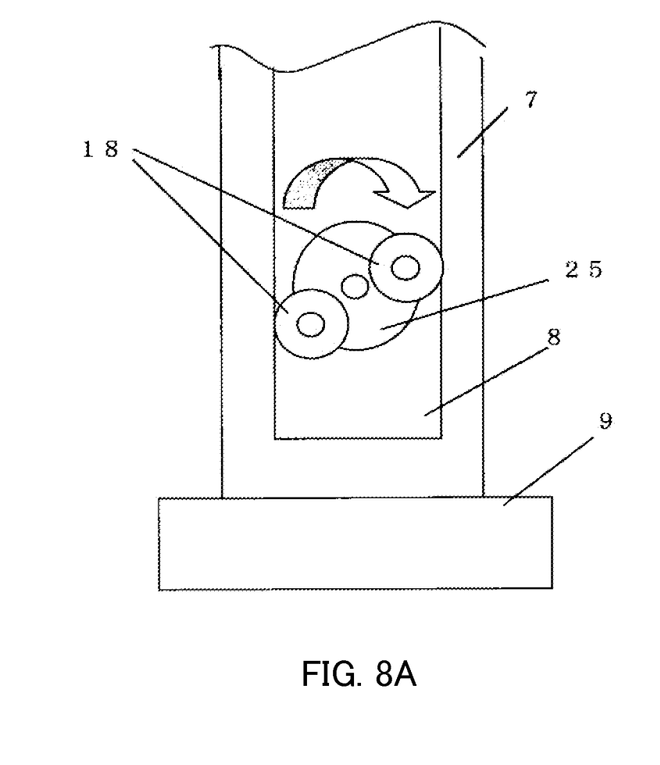
FIGS. 8A and 8B illustrates an example of the sliding contact state between the groove-shaped guide portion provided to the third arm and the protrusion of the first arm.
Figure 8B:
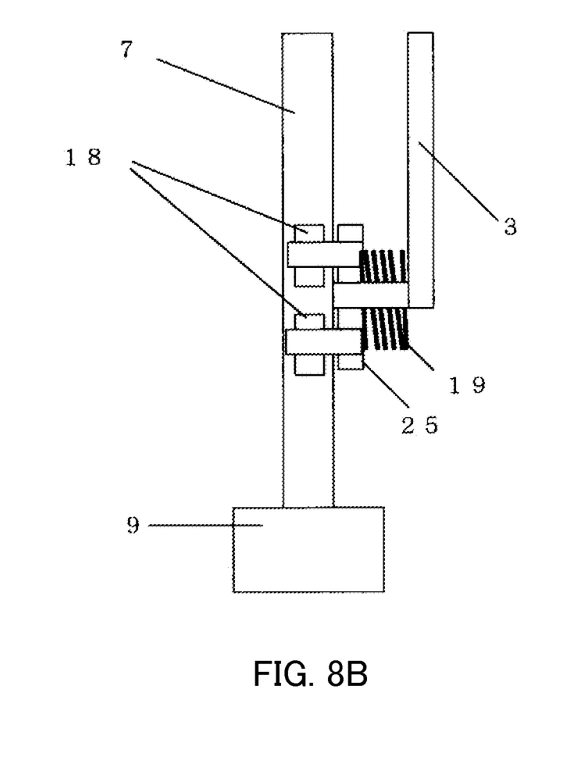

FIGS. 8A and 8B illustrate an example of the sliding contact state between groove-shaped guide portion 8 provided in third arm 7 and protrusion 13 provided at an end of first arm 3. The sliding contact state of protrusion 13 may be achieved with the configuration illustrated in FIGS. 8A and 8B instead of the configuration illustrated in FIG. 2. In the configuration illustrated in FIGS. 8A and 8B, rotation plate 25 rotatably attached to first arm 3 is rotated in one direction using elastic member 19 composed of, for example, a spring, and two or more bearings 18 are rotatably attached to rotation plate 25. A force in a direction in which bearings 18 are pressed against the inner wall of groove-shaped guide portion 8 is exerted on rotation plate 25 by elastic member 19, and thus bearings 18 are kept in contact with the inner wall of guide portion 8. Such a configuration is preferable since backlash can be prevented even when the width of guide portion 8 is non-uniform, and when the interval between two bearings 18 with respect to the width of guide portion 8 is slightly erroneous. It is also possible to coat the inner wall of groove-shaped guide portion 8 with low friction resin 17.

As described above, in the configuration illustrated in FIG. 1A to FIG. 8B, when first arm 3 fixed to rotational shaft 2 rotates about rotational shaft 2, first arm 3 and second arm 4 perform swing operation in opposite directions with the engagement between first gear 5 and second gear 6. In addition, third arm 7 performs swing operation on the basis of the position determined by the coupling part where third arm 7 and second arm 4 are coupled together, and guide portion 8 where protrusion 13 of first arm 3 can be translated while making sliding contact with guide portion 8. Accordingly, when motor 1 is driven into rotation to swing first arm 3 and second arm 4, ultrasound device 9 attached at an end of third arm 7 swings along a track having a curvature greater than that of a swing movement about an end of third arm 7.

Next, another example of the sliding contact state between third arm 7 and protrusion 13 provided at an end of first arm 3 is described.

Figure 9:
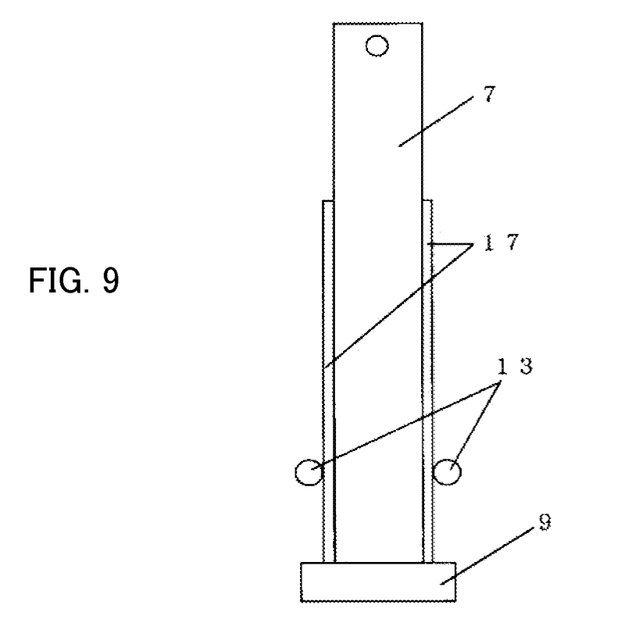
FIG. 9 illustrates another example of the sliding contact state between the groove-shaped guide portion provided to the third arm and the protrusion of the first arm.

FIG. 9 illustrates another example of the sliding contact state between third arm 7 and protrusion 13 provided at an end of first arm 3. The sliding contact state of protrusion 13 may be achieved with the configuration illustrated in FIG. 9 instead of the configuration illustrated in FIG. 2. In the configuration illustrated in FIG. 9, protrusion 13 is composed of two or more protrusions provided at an end of first arm 3, and third arm 7 is sandwiched by the protrusions. Also with this configuration, protrusions 13 smoothly slides on third arm 7, and therefore one or both of the contact surfaces between third arm 7 and protrusion 13 is preferably coated with low friction resin 17 composed of a fluorine resin. With such a configuration, the frictional resistance between the surfaces of third arm 7 and protrusion 13 in contact with each other is reduced. It is to be noted that, in the configuration illustrated in FIG. 9, third arm 7 may not be provided with groove-shaped guide portion 8.

Figure 10:
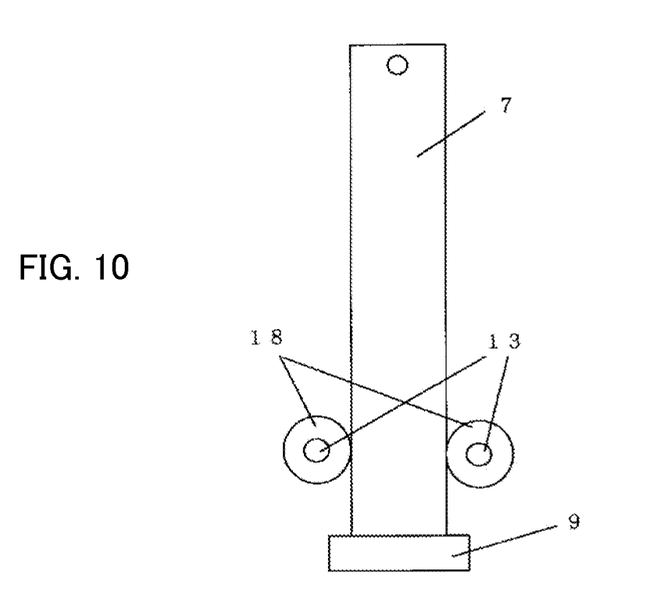
FIG. 10 illustrates another example of the sliding contact state between the groove-shaped guide portion provided to the third arm and the protrusion of the first arm.

FIG. 10 illustrates another example of the sliding contact state between third arm 7 and protrusion 13 provided at an end of first arm 3. The sliding contact state of protrusion 13 may be achieved with the configuration illustrated in FIG. 10 instead of the configuration illustrated in FIG. 2. In the configuration illustrated in FIG. 10, protrusion 13 is composed of two or more protrusions provided at an end of first arm 3 and third arm 7 is sandwiched by the protrusions. Further, protrusion 13 is provided with two or more bearings 18, thus reducing sliding movement resistance. It is to be noted that, in the configuration illustrated in FIG. 10, third arm 7 may not be provided with groove-shaped guide portion 8. It is also possible to coat the surface of third arm 7 with low friction resin 17.

Figure 11:
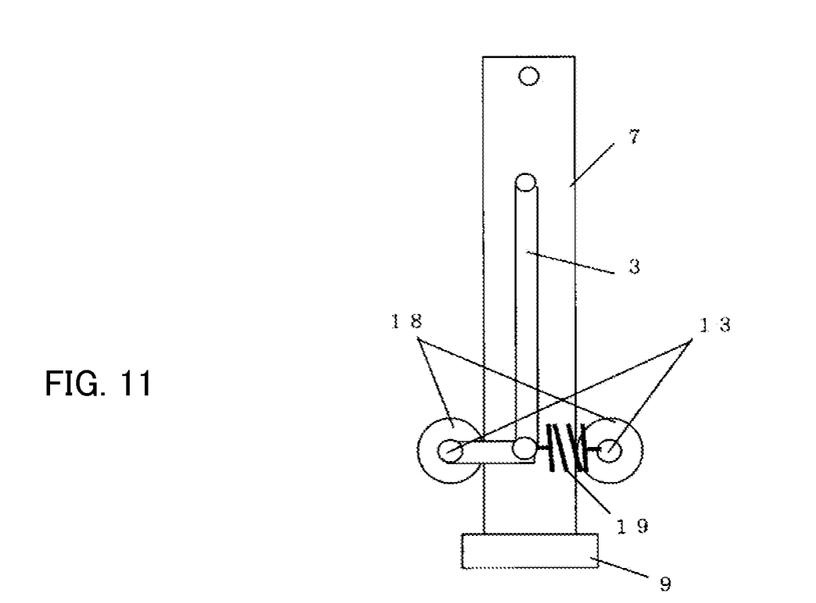
FIG. 11 illustrates another example of the sliding contact state between the groove-shaped guide portion provided to the third arm and the protrusion of the first arm.

FIG. 11 illustrates another example of the sliding contact state between third arm 7 and protrusion 13 provided at an end of first arm 3. The sliding contact state of protrusion 13 may be achieved with the configuration illustrated in FIG. 11 instead of the configuration illustrated in FIG. 2. In the configuration illustrated in FIG. 11, bearing 18 is rotatably connected with one of protrusions 13 of first arm 3, and bearing 18 connected with the other of protrusions 13 is connected such that bearing 18 is pulled by elastic member 19, and thus third arm 7 is sandwiched by two bearings 18 with the tensile stress of elastic member 19. As a result, it is possible to reduce variation in sliding movement resistance caused by variation in width of third arm 7 due to inconsistency in accuracy of machining for third arm 7. It is also possible to coat the surface of third arm 7 with low friction resin 17.

As described above, with the configurations illustrated in FIGS. 1A to 4 and FIGS. 9 and 10, when first arms 3 fixed to rotational shaft 2 rotates about rotational shaft 2, first arm 3 and second arm 4 perform swing operation in opposite directions with the engagement between first gear 5 and second gear 6. In addition, third arm 7 performs swing operation in accordance with the coupling with second arm 4 and the translatable sliding contact of protrusion 13 of first arm 3. Accordingly, when first arm 3 and second arm 4 are swung by driving motor 1 into rotation, ultrasound device 9 attached at an end of third arm 7 swings along a track having a curvature greater than that of a swing movement about an end of third arm 7. In addition, since third arm 7 is sandwiched by protrusions 13 from the both sides, third arm 7 can be easily and accurately worked by grinding or the like to achieve uniform width.

Figure 12:
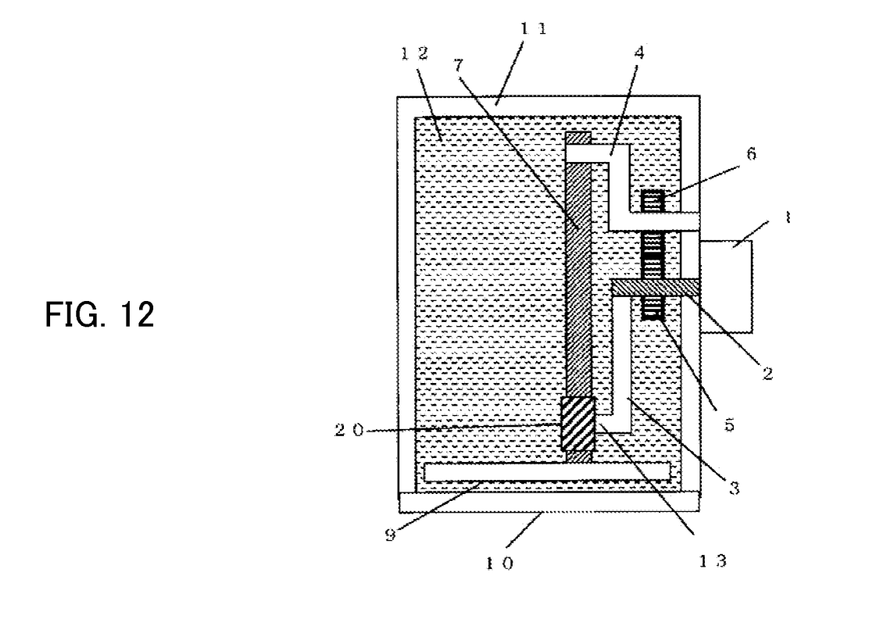
FIG. 12 illustrates another example of the sliding contact state between the groove-shaped guide portion provided to the third arm and the protrusion of the first arm.

FIG. 12 illustrates another example of the sliding contact state between third arm 7 and protrusion 13 provided at an end of first arm 3. The sliding contact state of protrusion 13 may be achieved with the configuration illustrated in FIG. 12 instead of the configuration illustrated in FIG. 2. In the configuration illustrated in FIG. 12, protrusion 13 provided at an end of first arm 3 has slide bearing 20. Slide bearing 20 can slide on third arm 7 along the longitudinal direction of third arm 7. Since first arm 3 is connected with slide bearing 20 such that first arm 3 is rotatable with respect to slide bearing 20, it is possible to achieve a smooth swing mechanism with only small sliding movement resistance and little backlash. It is to be noted that, in the configuration illustrated in FIG. 12, third arm 7 may not be provided with groove-shaped guide portion 8.

According to the configuration illustrated in FIG. 12, when first arms 3 fixed to rotational shaft 2 rotates about rotational shaft 2, first arm 3 and second arm 4 perform swing operation in opposite directions with the engagement between first gear 5 and second gear 6. In addition, third arm 7 performs swing operation in accordance with the coupling with second arm 4 and the translatable sliding contact of protrusion 13 of first arm 3. Accordingly, when first arm 3 and second arm 4 are swung by driving motor 1 into rotation, ultrasound device 9 attached at an end of third arm 7 swings along a track having a curvature greater than that of a swing movement about an end of third arm 7. In addition, smooth movement with reduced sliding movement resistance and little backlash can be achieved at low cost. In addition, when a bearing is rotatably used to fix slide bearing 20 to protrusion 13 of first arm 3, further smooth operation and reduction in mechanical load can be achieved.

Next, an attachment structure for attaching ultrasound device 9 to third arm 7, and operation of ultrasound device 9 will be described.

Figure 13:
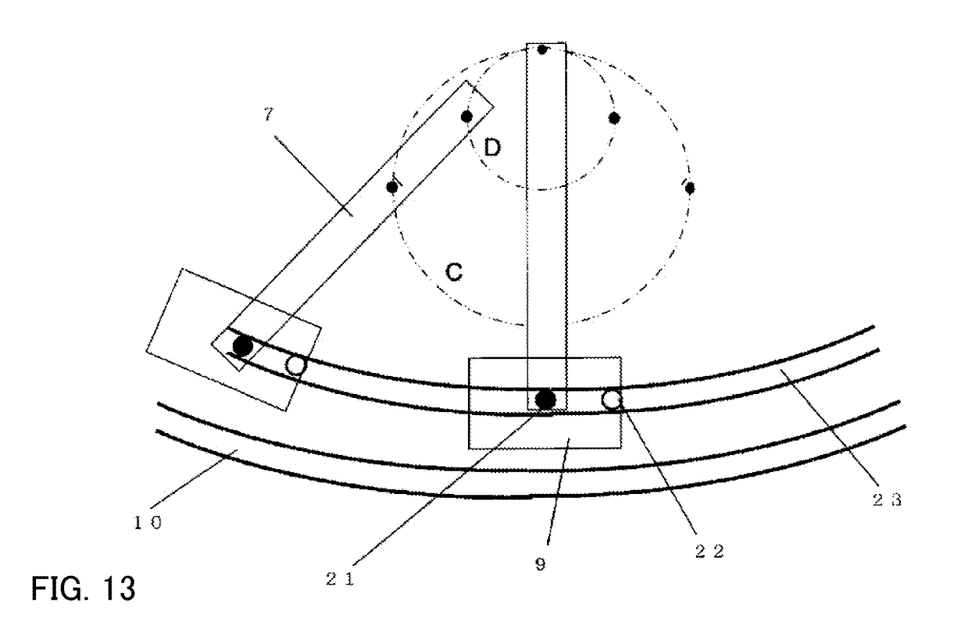
FIG. 13 describes operation and an example of an attachment structure of an ultrasound device.

FIG. 13 describes operation and an example of an attachment structure of ultrasound device 9. As illustrated in FIG. 13, ultrasound device 9 is attached to an end of third arm 7 such that ultrasound device 9 is rotatable about device rotational shaft 21. In addition, ultrasound device 9 is provided with guide shaft 22 which is rotatable integrally with ultrasound device 9 with respect to an end of third arm 7. Guide shaft 22 makes sliding contact with groove-shaped rail 23 provided to probe casing 11, window 10 or the like. This makes it possible to tilt ultrasound device 9, which transmits and receives ultrasound waves, relative to a living body in a desired direction. Since guide shaft 22 is fixed to ultrasound device 9, the orientation of ultrasound device 9 at the time when third arm 7 swings is determined by guide shaft 22. That is, ultrasound device 9 can be tilted such that ultrasound device 9 is always parallel to window 10, and thus, ultrasound waves radiated from ultrasound device 9 can be applied to window 10 such that the ultrasound waves are always perpendicular to window 10.

It is to be noted that groove-shaped rail 23 may be provided by designing a part of probe casing 11 or window 10 into a rail shape, or by attaching a rail-shaped component to probe casing 11 or window 10. In addition, the orientation of ultrasound device 9 can be set to a direction identical to the inclination of third arm 7 by fixing ultrasound device 9 to third arm 7. In this case, the above-mentioned device rotational shaft 21, guide shaft 22 and rail 23 may not be provided.

Figure 14:
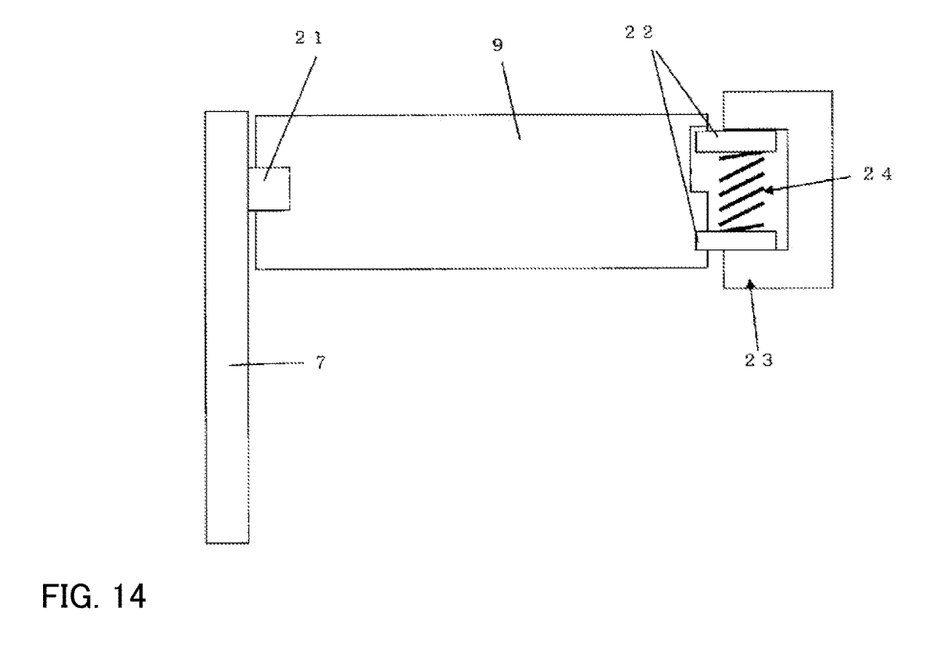
FIG. 14 describes operation and an example of the attachment structure of the ultrasound device.

FIG. 14 describes operation and an example of an attachment structure of ultrasound device 9. As illustrated in FIG. 14, ultrasound device 9 is attached to an end of third arm 7 such that ultrasound device 9 is rotatable about device rotational shaft 21. In addition, ultrasound device 9 is provided with two or more guide shafts 22 which are rotatable integrally with ultrasound device 9 with respect to an end of third arm 7. One of two guide shafts 22 is fixed to ultrasound device 9, and the other of guide shafts 22 is connected with guide shaft 22 fixed to ultrasound device 9 by second elastic member 24 composed of a spring or the like, and thus, with the repulsive force of second elastic member 24, two guide shafts 22 make sliding contact with groove-shaped rail 23 such that guide shafts 22 are sandwiched by groove-shaped rail 23. In this manner, it is possible to absorb backlash between groove-shaped rail 23 and two guide shafts 22 which occurs depending on the accuracy in working the components, and consequently, it is possible to reduce vibration and noise during the operation while stabilizing the tilted angle of ultrasound device 9 during the swing operation.

Figure 15:
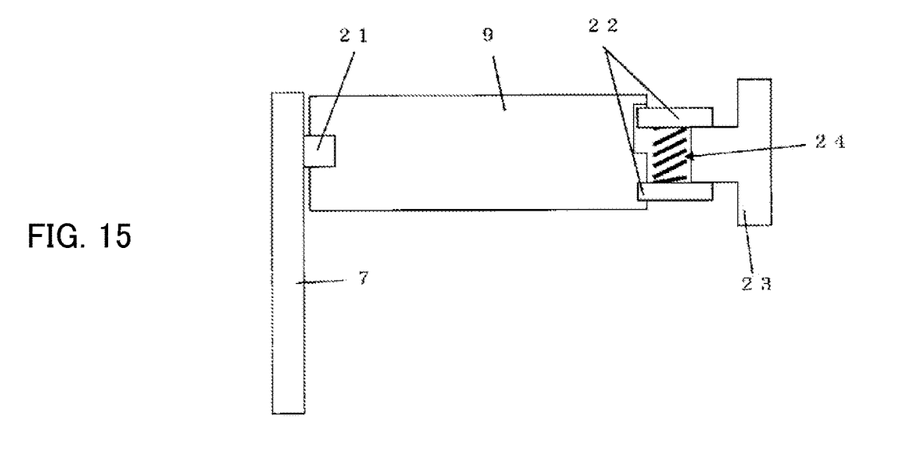
FIG. 15 describes operation and an example of the attachment structure of the ultrasound device.

FIG. 15 describes operation and an example of an attachment structure of ultrasound device 9. As illustrated in FIG. 15, ultrasound device 9 is attached to an end of third arm 7 such that ultrasound device 9 is rotatable about device rotational shaft 21. In addition, ultrasound device 9 is provided with two or more guide shafts 22 which are rotatable integrally with ultrasound device 9 with respect to an end of third arm 7. One of two guide shafts 22 is fixed to ultrasound device 9, and two guide shafts 22 make sliding contact with protruding rail 23 such that protruding rail 23 is sandwiched by guide shafts 22. In this manner, it is possible to absorb backlash between protruding rail 23 and two guide shafts 22 which occurs depending on the accuracy in working the components, and consequently, it is possible to stabilize the tilted angle of ultrasound device 9 during the swing operation while reducing vibration and noise during the operation. In addition, protruding rail 23 can be relatively readily worked when it is produced by machining or metal molding.

Figure 16:
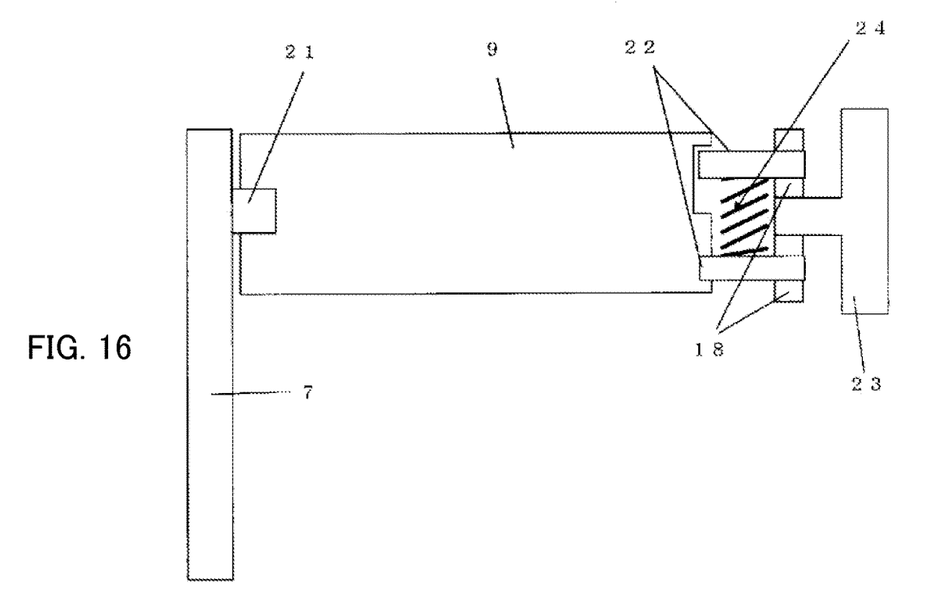
FIG. 16 describes operation and an example of the attachment structure of the ultrasound device.

FIG. 16 describes operation and an example of an attachment structure of ultrasound device 9. As illustrated in FIG. 16, ultrasound device 9 is attached to an end of third arm 7 such that ultrasound device 9 is rotatable about device rotational shaft 21. In addition, ultrasound device 9 is provided with two or more guide shafts 22 which are rotatable integrally with ultrasound device 9 with respect to an end of third arm 7. One of two guide shafts 22 is fixed to ultrasound device 9, and the other of guide shafts 22 is connected with guide shaft 22 fixed to ultrasound device 9 with second elastic member 24 composed of a spring or the like, and thus, with the absorbing force of second elastic member 24, two guide shafts 22 make sliding contact with protruding rail 23 such that two guide shafts 22 sandwich protruding rail 23. Bearing 18 is provided at an end of each guide shaft 22. With this configuration, it is possible to further reduce the frictional resistance of the sliding movement between protruding rail 23 and guide shaft 22, and to achieve smooth movement and reduced driving load of motor 1.

Figure 17:
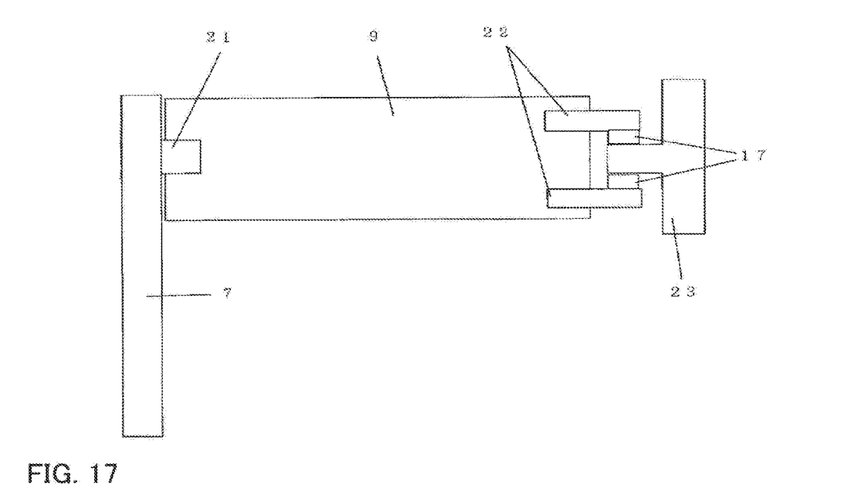
FIG. 17 describes operation and an example of the attachment structure of the ultrasound device.

FIG. 17 describes operation and an example of an attachment structure of ultrasound device 9. As illustrated in FIG. 17, ultrasound device 9 is attached to an end of third arm 7 such that ultrasound device 9 is rotatable about device rotational shaft 21. In addition, ultrasound device 9 is provided with two or more guide shafts 22 which are rotatable integrally with ultrasound device 9 with respect to an end of third arm 7. Two guide shafts 22 make sliding contact with protruding rail 23 such that protruding rail 23 is sandwiched by guide shafts 22, and a material which reduces the frictional resistance between the surfaces of guide shaft 22 and rail 23 in contact with each other, for example, low friction resin 17 such as a fluorine resin, is attached to one or both of guide shaft 22 and rail 23. With this configuration, it is possible to reduce the frictional resistance of the sliding movement between protruding rail 23 and guide shaft 22, and, while achieving smooth movement and reduced driving load of motor 1, it is possible to achieve size reduction and cost reduction in comparison with the configuration adopting a bearing.

With the configuration described with reference to FIGS. 13 to 16 in which rail 23 is provided, the ultrasound device can be tilted in a direction perpendicular to the window or other desired directions. In addition, by appropriately changing the rail shape, the angle at which ultrasound waves are emitted and received to and from a living body can be freely set, and the angle of the device can be set in accordance with the diagnosis such that the device moves in parallel to a living body, or along an arc with respect to a living body.

As described, according to the above-mentioned embodiment, the apparent rotational radius along which an ultrasound device moves can be increased, and downsizing can be achieved by shortening the arm of the swing movement. In addition, unlike the above-described conventional configuration in which an ultrasound device is translated with a wire and pulleys, and spaces corresponding to the diameter of the pulleys are formed at the both ends of a scan region, such spaces can be practically eliminated, and the scan region can be substantially increased with respect to the portion that makes contact with a patient. In addition, since the ultrasound probe can be downsized while achieving a large scan region, the ultrasound probe can be easily brought into close contact with a living body.

In addition, the ultrasound probe may be a mechanical ultrasound probe that mechanically scans an object with a swing mechanism in which ultrasound device 9 is a single device. Alternatively, the ultrasound probe may be an ultrasound probe in which ultrasound device 9 is an electron scan type ultrasound device, and ultrasound devices are disposed so as to perform electron scanning in a direction orthogonal to a mechanical swing direction, whereby a three-dimensional ultrasound image is obtained by electron scanning and by scanning with mechanical swing.

While the invention made by the present inventor has been specifically described based on the preferred embodiments, it is not intended to limit the present invention to the above-mentioned preferred embodiments but the present invention may be further modified within the scope and spirit of the invention defined by the appended claims.

This application is entitled to and claims the benefit of Japanese Patent Application No. 2012-163376 filed on Jul. 24, 2012, the disclosure of which including the specification, drawings and abstract is incorporated herein by reference in its entirety.

INDUSTRIAL APPLICABILITY

The present invention is suitable for a small-sized hand carry type ultrasound probe that obtains a three-dimensional tomogram in a living body by a mechanical translation or swing movement in a direction orthogonal to the direction of an electrical scanning of an array type device that obtains a tomographic image by performing an electrical scan with piezoelectric elements laid out in a belt form. In addition, a small-sized and lightweight device can be provided not only in the hand carry type ultrasound probe but also in a standing type ultrasound device that scans a wide area on the body surface.

REFERENCE SIGNS LIST

1 Motor
2 Rotational shaft
3 First arm
4 Second arm
5 First gear
6 Second gear
7 Third arm
8 Guide portion
9 Ultrasound device
10 Window
11 Probe casing
12 Acoustic coupling liquid
13 Protrusion
14 First pulley
15 Second pulley
16 Belt
17 Low friction resin
18 Bearing
19 Elastic member
20 Slide bearing
21 Device the rotational shaft
22 Guide shaft
23 Rail
24 Second elastic member
25 Rotation plate

The invention claimed is:

1. An ultrasound probe comprising:
a probe casing in which acoustic coupling liquid is sealed;
a motor fixed to the probe casing;
a first arm fixed to a first rotational shaft, and configured to rotate along with rotation of the first rotational shaft;
a protrusion provided to the first arm;
a first rotation transmission section attached to the first rotational shaft;
a second rotation transmission section engaged with the first rotation transmission section, and configured to rotate when the first rotation transmission section rotates in a direction opposite to a direction in which the first rotation transmission section rotates;
a second rotational shaft fixed to the second rotation transmission section, and configured to serve as a rotational shaft of the second rotation transmission section;
a second arm fixed to the second rotational shaft, and configured to rotate along with rotation of the second rotational shaft;
a third arm attached to the second arm such that the third arm is rotatable with respect to the second arm; and
an ultrasound device connected with the third arm, wherein:
the first arm, the second arm and the third arm are located in the probe casing;
the motor is connected with the first rotational shaft or the second rotational shaft;
the first rotational shaft or the second rotational shaft connected with the motor rotates along with rotation of the motor; and
the protrusion provided to the first arm is connected with the third arm such that the protrusion provided to the first arm is slidable along a longitudinal direction of the third arm.

2. The ultrasound probe according to claim 1, wherein:
the second arm includes a first end and a second end different from the first end;
the first end is connected with the probe casing such that the first end is rotatable with respect to the probe casing;
the second end is connected with a first end portion of the third arm;
the ultrasound device is connected with an end of a second end portion of the third arm different from the first end portion of the third arm; and
the protrusion is located between the first end portion and the ultrasound device in the third arm.

3. The ultrasound probe according to claim 1, wherein:
the third arm is provided with a guide portion extending along the longitudinal direction of the third arm; and
the protrusion is in sliding contact with the guide portion.

4. The ultrasound probe according to claim 3, wherein:
the guide portion is a part that is obtained by forming at least a portion of the third arm into a groove shape; and
the protrusion is in sliding contact with an inner wall of the guide portion having the groove shape.

5. The ultrasound probe according to claim 4, wherein the inner wall of the guide portion having the groove shape or the protrusion, or both is provided with a material that reduces a frictional resistance between a surface of the inner wall of the guide portion having the groove shape and a surface of the protrusion in contact with each other.

6. The ultrasound probe according to claim 1, wherein the protrusion is provided with a bearing that is rotatable with respect to the protrusion.

7. The ultrasound probe according to claim 4, further comprising:
an elastic member attached to the first arm;
a rotatable rotation plate on which a rotational force in one direction is exerted by the elastic member; and
at least two bearings rotatably provided to the rotation plate, wherein
the at least two bearings are configured to make contact with the inner wall of the guide portion having the groove shape.

8. The ultrasound probe according to claim 1, wherein:
the protrusion includes at least two protrusions; and
the at least two protrusions sandwich the third arm.

9. The ultrasound probe according to claim 8, wherein each of the at least two protrusions or the third arm, or both is provided with a material that reduces a frictional resistance between the surface of the third arm and surfaces of the at least two protrusions in contact with each other.

10. The ultrasound probe according to claim 8, wherein the at least two protrusions are each provided with a bearing.

11. The ultrasound probe according to claim 10, wherein the at least two protrusions pull against each other with an elastic member therebetween.

12. The ultrasound probe according to claim 1, wherein the protrusion includes a slide bearing that is slidable on the third arm.

13. The ultrasound probe according to claim 1, wherein the first rotation transmission section and the second rotation transmission section are each composed of a gear.

14. The ultrasound probe according to claim 1, wherein:
the first rotation transmission section and the second rotation transmission section are each composed of a pulley; and
a belt is wound around the first rotation transmission section and the second rotation transmission section such that the belt intersects between the first rotation transmission section and the second rotation transmission section.

15. The ultrasound probe according to claim 1, wherein the first rotation transmission section and the second rotation transmission section are housed in the probe casing.

16. The ultrasound probe according to claim 1, wherein:
the ultrasound device is connected with the third arm such that the ultrasound device is rotatable with respect to the third arm;
the ultrasound device is connected with a first guide shaft;
a rail is provided in the probe casing; and
the first guide shaft is in contact with the rail such that the first guide shaft is movable along the rail.

17. The ultrasound probe according to claim 16, wherein:
the rail has a groove shape; and
the first guide shaft is located in a groove having the groove shape.

18. The ultrasound probe according to claim 16, further comprising a second guide shaft connected with the first guide shaft with an elastic member therebetween, wherein the first guide shaft and the second guide shaft are sandwiched by the rail.

19. The ultrasound probe according to claim 16, further comprising a second guide shaft connected with the first guide shaft with an elastic member therebetween, wherein:
the rail includes a protrusion; and
the first guide shaft and the second guide shaft sandwich the protrusion of the rail.

20. The ultrasound probe according to claim 16, wherein, in the first guide shaft, a part that makes contact with the rail is provided with a bearing.

21. The ultrasound probe according to claim 16, wherein the first guide shaft or the rail or both is provided with a resin material that reduces a frictional resistance between the first guide shaft and the rail in contact with each other.

22. The ultrasound probe according to claim 1, wherein:
the ultrasound device is an electron scan type device; and
the ultrasound device mechanically swings in a direction orthogonal to a direction of an electron scan of the ultrasound device.

* * * * *